May 24, 1960 F. W. ANDERSON Plant Pat. 1,946

PEACH TREE

Filed Aug. 14, 1959

WITNESS

Addison E. Avery

INVENTOR

Frederic W. Anderson

Webster & Webster

ATTYS.

United States Patent Office

Plant Pat. 1,946
Patented May 24, 1960

1,946

PEACH TREE

Frederic W. Anderson, Merced, Calif., assignor to Stark Bro's Nurseries and Orchards Co., Louisiana, Mo., a corporation of Missouri Filed Aug. 14, 1959, Ser. No. 833,901

1 Claim. (Cl. 47—62)

This invention relates to a new and distinct variety of peach tree which bears freestone to semi-freestone fruit having flesh which is yellow adjacent the stone and red adjacent the skin; the skin being yellow ground color overspread to a major extent with red. The variety is of the type embraced by group 33 of the classification by Caillavet and Souty, Monographie des Principales Variétés de Pêchers, 1950 edition, page 45.

The fruit of the present variety ripens approximately with the Merrill Gem peach (United States Plant Patent No. 868) and which is the pollen parent, but—in comparison—is produced more abundantly, requires less chilling, is more uniform in size and shape, has less defective fruit at harvest, and is of better eating quality.

As compared with the Gold Dust peach (United States Plant Patent No. 1,144) the fruit of the present variety is larger, firmer of flesh, and has more red exterior color.

The herein claimed variety of peach tree was originated by me in my experimental orchard, located near Merced, California, in the following manner:

Pollen from Merrill Gem peach blossoms was applied to the pistils of Sun Grand nectarine (United States Plant Patent No. 974) blossoms, and a number of seeds from the resultant fruit were planted and grown to the point of bearing; all such progeny being peaches, and from which the present variety was selected, as its fruit evidenced the novel and desirable characteristics hereinbefore described.

Subsequent to its origination and selection, as above, the variety was asexually reproduced by me as top-workings on mature orchard trees in my experimental orchard located as aforesaid; such reproductions having been found to run true in all respects.

Figures 1, 2:
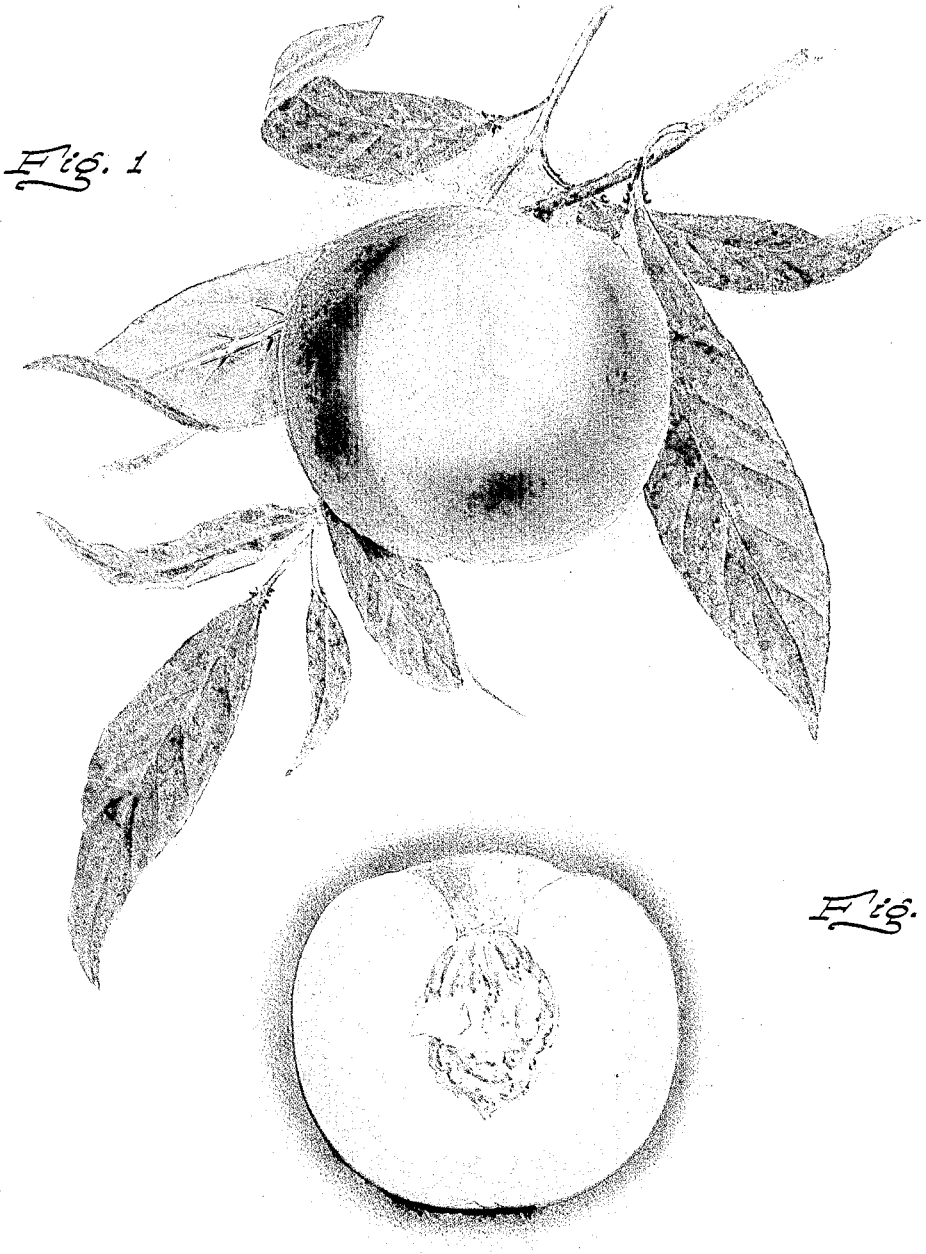
Fig. 1 is an elevation showing one of the peaches, together with twigs and leaves.
Fig. 2 is a sectional elevation of one of the peaches with the stone remaining in place.

Referring to pomological details of this new and distinct variety of peach tree and its fruit, the following is an outline description thereof; all major color plate identifications being by reference to Maerz and Paul Dictionary of Color:

Tree:
- *Size.*—Large to medium.
- *Vigor.*—Vigorous.
- *Form.*—Upright to spreading.
- *Production.*—Productive.
- *Bearing.*—Regular bearer.

Trunk: Size—stocky to medium.

Leaves:
- *Size.*—Large to medium—average length and width.
- *Margin.*—Glandular; crenate.
- *Petiole.*—Long to medium; thick to medium.

- *Glands.*—Average number—usually two on petiole and two or more on blade. Large to medium; reniform.
- *Color.*—Top side—medium green (22–L–9). Under size—lighter green (22–J–5).

Flower buds: Size—large to medium.

Flowers: Blooming period (1958).
- *Date of first bloom.*—March 10th.
- *Date of full bloom.*—March 20th. Medium compared with other varieties.
- *Size.*—Medium.
- *Type.*—Non-showy.

Fruit:
- *Maturity when described.*—Eating ripe—June 30, 1958.
- *Date of first picking.*—June 23, 1958.
- *Date of last picking.*—July 4, 1958.
- *Size.*—Uniform. Average diameter axially—2½". Average transversely in suture plane—2¾".
- *Form.*—Uniform; symmetrical; globose
- *Suture.*—Shallow. Extends from base to apex, with slight depression beyond pistil point.
- *Cavity.*—Rounded. Average depth—½". Average breadth—⅝".
- *Base.*—Rounded.
- *Apex.*—Short; depressed.
- *Pistil point.*—Apical.

Skin:
- *Thickness.*—Thick to medium.
- *Tendency to crack.*—None noted.
- *Down.*—Moderate.
- *Color.*—Yellow (10–K–6), overspread to a major extent with red (3–C–11 to 3–J–11) in the lightest area, shading therefrom to darker red (7–L–6).

Flesh:
- *Texture.*—Firm.
- *Ripens.*—Even.
- *Flavor.*—Sub-acid.
- *Aroma.*—Distinct.
- *Eating quality.*—Good.
- *Color.*—Yellow (9–K–3 to 9–B–8) adjacent the stone, and red (3–J–11) adjacent the skin.

Stone:
- *Type.*—Free to semi-free.
- *Size.*—Medium.
- *Color.*—Buff (9–C–7).

Use: Market.

Keeping quality: Good.

Shipping quality: Good.

The tree and its fruit herein described may vary in slight detail due to climatic and soil conditions under which the variety may be grown; the present description being of the variety as grown in the Central Valley of California.

The following is claimed:

A new and distinct variety of peach tree, as illustrated and described, which bears freestone to semi-freestone fruit having flesh which is yellow adjacent the stone and red adjacent the skin, the skin being yellow overspread to a major extent with red; such fruit ripening approximately with the Merrill Gem peach, but—in comparison—is produced more abundantly, requires less chilling, is more uniform in size and shape, has less defective fruit at harvest, and is of better eating quality; and further—in comparison with the Gold Dust peach—is larger, firmer of flesh, and has more red exterior color.

No references cited.